United States Patent [19]

Baudouin et al.

[11] 4,412,075

[45] Oct. 25, 1983

[54] PROCESS FOR THE PREPARATION OF QUINOLIN-4-ONES

[75] Inventors: Michel Baudouin, St-Fons; Michel Desbois, Rillieux la Pape, both of France

[73] Assignee: Rhone-Poulenc Sante, Courbevoie, France

[21] Appl. No.: 339,725

[22] Filed: Jan. 15, 1982

[30] Foreign Application Priority Data

Jan. 16, 1981 [FR] France ............................ 81 00762

[51] Int. Cl.³ .......................................... C07D 215/22
[52] U.S. Cl. ................................................. 546/153
[58] Field of Search ........................................ 546/153

[56] References Cited

U.S. PATENT DOCUMENTS 2,558,211  6/1951  Elderfield et al. .................. 546/153
3,116,295  12/1963  Zerweck et al. ...................... 546/49
3,567,732  3/1971  Joly et al. ......................... 546/153 X

OTHER PUBLICATIONS

I. G. Farbenind A. G., Chemical Abstracts, vol. 44, 4991⁵, (1937), (abstract of Fr. 806,715, 12/23/36).
Meyer et al., Chemical Abstracts, vol. 73, 66317x, (1970).
Takeshita et al., Chemical Abstracts, vol. 83, 149103g, (1975).

*Primary Examiner*—Diana G. Rivers

*Attorney, Agent, or Firm*—Stevens, Davis, Miller & Mosher

[57] ABSTRACT 1,2,3,4-Tetrahydroquinolin-4-ones of the formula:

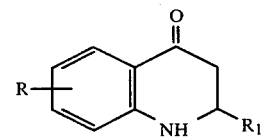

wherein R represents a hydrogen or halogen atom, an alkyl radical (1 to 4 carbon atoms), an alkoxy radical (1 to 4 carbon atoms) or the trifluoromethyl radical, and $R_1$ represents a hydrogen atom, an alkyl radical (1 to 4 carbon atoms) or the trifluoromethyl radical, are prepared by cyclizing a 3-anilinopropionic acid of the formula:

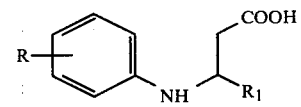

(wherein R and $R_1$ are as hereinbefore defined) in a mixture of hydrofluoric acid and boron trifluoride.

The quinolinone products are useful intermediates in the synthesis of therapeutically active substances.

10 Claims, No Drawings

PROCESS FOR THE PREPARATION OF QUINOLIN-4-ONES

DESCRIPTION

The present invention relates to a new process for the preparation of 1,2,3,4-tetrahydroquinolin-4-ones of the general formula:

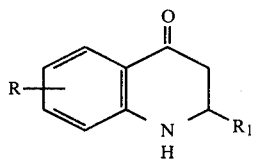

wherein R represents a hydrogen atom or a substituent selected from halogen atoms, straight- or branched-chain alkyl radicals containing 1 to 4 carbon atoms, straight- or branched-chain alkoxy radicals containing 1 to 4 carbon atoms, and the trifluoromethyl radical, and $R_1$ represents a hydrogen atom or a straight- or branched-chain alkyl radical containing 1 to 4 carbon atoms or the trifluoromethyl radical, which are particularly useful as intermediates in the synthesis of therapeutically active substances.

It is known to prepare 1,2,3,4-tetrahydrolquinolin-4-ones of general formula (I) by cyclising a 3-anilino-propionic acid, the amino group of which is optionally substituted, by means of sulphuric acid, phosphorus pentoxide or phosphoric or polyphosphoric acid.

It is also known, for example from French Patent 806715, to cyclise a 3-arylaminopropionitrile which is substituted or unsubstituted on the nitrogen by operating in the presence of aluminium chloride; the cyclisation can be carried out using other agents such as boron trifluoride, aluminium bromide, the halides of titanium, tin, arsenic or antimony, or the oxyhalides of phosphorus ($POCl_3$), ferric chloride, or hydrogen halides or sulphuric acid.

It has now been found that the 1,2,3,4-tetrahydroquinolin-4-ones of general formula (I) can be obtained with virtually quantitative yields by cyclising a 3-anilinopropionic acid of the general formula:

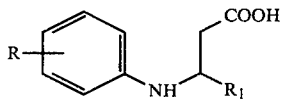

(wherein R and $R_1$ are as hereinbefore defined) in the presence of a mixture of hydrofluoric acid and boron trifluoride; it is this finding which forms the subject of the present invention.

This result is all the more surprising and unexpected as the cyclisation of an acid of general formula (II) does not take place in the presence of hydrofluoric acid alone or of boron trifluoride alone, and because the corresponding 3-anilinopropionitrile in the presence of a mixture of hydrofluoric acid and boron trifluoride does not lead to the quinolin-4-one.

In order to carry out the process according to the present invention it is particularly advantageous to heat a solution, saturated with boron trifluoride, of an acid of general formula (II) in hydrofluoric acid, preferably under pressure.

The acid of general formula (II) can be dissolved in hydrofluoric acid in an amount of 1 mol of acid of general formula (II) per 15 to 50 mols of hydrofluoric acid.

To obtain a complete conversion of the acid of general formula (II), it is necessary to introduce in the reaction at least 2 mols of boron trifluoride per mol of acid of general formula (II). The boron trifluoride can be introduced either all at once at the start of the reaction, or gradually during the reaction so as to maintain a partial pressure of between 1 and 30 bars.

When an acid of general formula (II) is used wherein a substituent R is in the meta-position relative to the amino group and represents a halogen atom or an alkyl or alkoxy radical, the 1,2,3,4-tetrahydroquinolin-4-one of general formula (I) substituted in the 7-position is obtained virtually free of the isomer substituted in the 5-position, which it is theoretically possible to obtain.

When the acid of general formula (II) is 3-m-chloroanilinopropionic acid, the results are particularly satisfactory. In fact, whereas according to French Pat. No. 1514280 the cyclisation of 3-m-chloroanilinopropionic acid by means of polyphosphoric acid at a temperature of about 100° C. leads to a mixture of virtually equal proportions of 5-chloro-1,2,3,4-tetrahydroquinolin-4-one and 7-chloro-1,2,3,4-tetrahydroquinolin-4-one, the constituents of which mixture must be separated in order for them to be used subsequently, the process according to the invention makes it possible to obtain 7-chloro-1,2,3,4-tetrahydroquinolin-4-one with a proportion of the 5-chloro isomer which can be less than 1%.

In this process, the best results are obtained if the cyclisation is carried out in a reaction mixture consisting of a solution, saturated at 20° C. with boron trifluoride, of 3-m-chloroanilinopropionic acid in hydrofluoric acid, in amounts of one molecule of 3-m-chloroanilinopropionic acid per 15 to 50 mols of hydrofluoric acid, under a pressure of between 2 and 16 bars, preferably about 12 bars, and at a temperature between 60° and 100° C., preferably around 80° C., for about 20 hours. Under these conditions, the degree of conversion is of the order of 100% and the proportion of 5-chloro-1,2,3,4-tetrahydroquinolin-4-one is less than 1%.

The 1,2,3,4-tetrahydroquinolin-4-one of general formula (I) obtained in accordance with the process of the present invention can be isolated from the reaction mixture in accordance with the usual methods. However, it is particularly advantageous to be able to recycle the hydrofluoric acid and the boron trifluoride used. For this purpose, it is possible to adopt the following procedure:

when the reaction has ended, the reaction mixture can be cooled and then degassed, which makes it possible to recover the major part of the boron trifluoride not combined with the organic products;

the hydrofluoric acid is then distilled, optionally after the addition of an organic solvent such as chlorobenzene or carbon tetrachloride; under these conditions, the quinolinone partially salified by the tetrafluoroboric acid is in suspension in the solvent; and the quinolinone is finally displaced from its salt by the addition of a base such as ammonia, and is obtained in solution in the solvent, the insoluble salt of the tetrafluoroboric acid and the base being filtered off.

The 1,2,3,4-tetrahydroquinolin-4-one of general formula (I) is isolated, after concentration if necessary of its solution, and is separated by filtration or decantation.

The 1,2,3,4-tetrahydroquinolin-4-one of general formula (I) so obtained can be purified by applying the usual methods such as crystallisation or chromatography.

The acids of general formula (II) used as starting materials can be obtained by reacting an appropriately substituted aniline with an acid of the general formula $$R_1—CH=CH—COOH \quad (III)$$

wherein $R_1$ is as hereinbefore defined. The reaction is generally carried out in water at a temperature between 70° and 100° C., the aniline being used in excess relative to the acid of general formula (III). The reaction time is generally between 1 and 4 hours.

The 1,2,3,4-tetrahydroquinolin-4-ones of general formula (I) are particularly useful as intermediates in the synthesis of therapeutically active substances such as chloroquine, glafenine, antrafenine or amodiaquin. More particularly, 7-chloro-1,2,3,4-tetrahydroquinolin-4-one can be converted to chloroquine by condensing it with 4-diethylamino-1-methylbutylamine in the presence of air, in accordance with the process described by W. S. Johnson and B. G. Buell, J. Amer. Chem. Soc., 74, 4513 (1952).

The following Examples, which are given without implying a limitation, show how the invention can be put into practice.

EXAMPLE 1

3-m-Chloroanilinopropionic acid (94.5% pure; 10 g) is introduced into a stainless steel reactor containing liquid hydrofluoric acid (50 g) cooled to 5° C. The solution is saturated with gaseous boron trifluoride. For this purpose, the contents of the reactor are kept at 20° C. and then saturated with gaseous boron trifluoride under a pressure of 12 bars for 1 hour. The reactor is subsequently closed and then heated at 80° C. for 20 hours.

During the heating, the pressure initially rises to 20 bars and then falls progressively until it stabilises at about 16 bars. The reactor is subsequently cooled to 10° C. and then opened so as to allow the boron trifluoride to escape. The reddish liquid obtained is poured into a mixture of water and ice. After extraction with chloroform (3×100 cc), the organic layer is washed with water (several times 100 cc) until the pH of the washings is between 3 and 4, and is then dried over sodium sulphate. After filtration and concentration to dryness under reduced pressure (10 mm Hg; 1.33 kPa), crystalline 7-chloro-1,2,3,4-tetrahydroquinolin-4-one (9 g) is obtained, the purity of which is 94.5% as determined by gas phase chromatography.

The degree of conversion is 100% and the yield relative to the 3-m-chloroanilinopropionic acid is 99%.

The proportion of the 5-chloro isomer is about 0.7% as determined by gas phase chromatography.

3-m-Chloroanilinopropionic acid used as starting material can be prepared in the following manner:

A solution of acrylic acid (72.05 g) in water (100 cc) is added in the course of 10 minutes to a mixture of m-chloroaniline (510.3 g) and water (150 cc), kept under an argon atmosphere and stirred at 80° C. The reaction mixture consists of two phases and is kept at 80° C. for 3 hours, whilst stirring, and then cooled to 20° C. After decantation, the aqueous phase (upper layer) is discarded. A 2.6 N aqueous solution of sodium hydroxide (423 cc) is added to the organic phase, whilst stirring and keeping the temperature at 20° C. After decantation, the organic phase consisting of m-chloroaniline (303 g) is separated. The aqueous phase (850 cc) is extracted with diethyl ether (6×450 cc in succession).

The aqueous phase, from which the ether is removed by evaporation under reduced pressure (20 mm Hg; 2.7 kPa), is acidified by adding 50% (by weight) sulphuric acid (105 g). The final pH is 3.5 (isoelectric point). The temperature increases from 22° to 33° C. and the mixture is then heated to 40° C. After settling, the following are separated:

a lower organic phase (208.8 g) consisting of molten 3-m-chloroanilinopropionic acid saturated with water (8.6% of water), and an upper aqueous phase (601 g) containing 3-m-chloroanilinopropionic acid (2.28 g) and sodium sulphate (156 g).

The organic phase is heated for 1 hour at 80° C. under reduced pressure (20 mm Hg; 2.7 kPa). This yields a product (195.4 g) containing 94% of 3-m-chloroanilinopropionic acid and 2.3% of water.

EXAMPLE 2

3-o-Trifluoromethylanilinopropionic acid (23.3 g) is introduced into a stainless reactor containing liquid hydrofluoric acid (100 g) cooled to 5° C. The solution is saturated with gaseous boron trifluoride. For this purpose, the contents of the reactor are kept at 20° C. and then saturated with gaseous boron trifluoride under a pressure of 17 bars for 1 hour. The reactor is subsequently closed and then heated at 80° C. for 19 hours.

The reaction mixture is then treated under the conditions of Example 1. This yields 8-trifluoromethyl-1,2,3,4-tetrahydroquinolin-4-one (13.9 g), the purity of which is 99% as determined by gas phase chromatography.

The degree of conversion is 68.7% and the yield is of the order of 95% relative to the 3-o-trifluoromethylanilinopropionic acid converted.

EXAMPLE 3

3-m-Chloroanilinobutanoic acid (21.4 g) is introduced into a stainless steel reactor containing liquid hydrofluoric acid (100 g) cooled to 5° C. The solution is saturated with gaseous boron trifluoride. For this purpose, the contents of the reactor are kept at 20° C. and then saturated with gaseous boron trifluoride under a pressure of 10 bars for 1 hour. The reactor is subsequently closed and then heated at 82° C. for 24 hours.

The reaction mixture is then treated under the conditions of Example 1. This yields 7-chloro-2-methyl-1,2,3,4-tetrahydroquinolin-4-one (18.3 g), the purity of which is 95% as determined by gas phase chromatography.

The degree of conversion is 93.5% and the yield is about 100% relative to the 3-m-chloroanilinobutanoic acid converted.

The proportion of the 5-chloro isomer is less than 1% as determined by gas phase chromatography and nuclear magnetic resonance.

EXAMPLE 4

3-m-Methylanilinopropionic acid (18.5 g) is introduced into a stainless steel reactor containing liquid hydrofluoric acid (100 g) cooled to 5° C. The solution is saturated with gaseous boron trifluoride. For this purpose, the contents of the reactor are kept at 20° C. and then saturated with gaseous boron trifluoride under a pressure of 11 bars for 1 hour. The reactor is then heated at 82° C. for 23 hours.

The reaction mixture is then treated under the conditions of Example 1. This yields 7-methyl-1,2,3,4-tetrahydroquinolin-4-one (16.6 g), the purity of which is 96% as determined by gas phase chromatography.

The degree of conversion is about 100% and the yield is about 100% relative to the 3-m-methylanilinopropionic acid converted.

The proportion of the 5-methyl isomer is less than 1% as determined by gas phase chromatography and nuclear magnetic resonance.

We claim:

1. A process for the preparation of a 1,2,3,4-tetrahydroquinolin-4-one of the general formula:

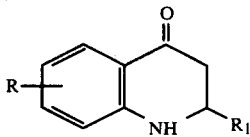

(wherein R represents a hydrogen atom or a substituent selected from halogen atoms, straight- or branched-chain alkyl radicals containing 1 to 4 carbon atoms, straight- or branched-chain alkoxy radicals containing 1 to 4 carbon atoms, and the trifluoromethyl radical, and $R_1$ represents a hydrogen atom, a straight- or branched-chain alkyl radical containing 1 to 4 carbon atoms or the trifluoromethyl radical) which comprises cyclizing a 3-anilinopropionic acid of the general formula:

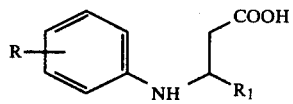

(wherein R and $R_1$ are as hereinbefore defined) in a mixture of hydrofluoric acid and boron trifluoride, and isolating the quinolinone product obtained.

2. A process according to claim 1 which comprises heating a solution, saturated with boron trifluoride, of the 3-anilinopropionic acid in hydrofluoric acid at a temperature between 20° and 120° C. optionally under pressure, and isolating the quinolinone product obtained.

3. A process according to claim 2 in which the reaction is carried out under a pressure of between 1 and 30 bars.

4. A process according to claim 1 in which at least 2 mols of boron trifluoride are used per mol of 3-anilinopropionic acid.

5. A process according to claim 1, 2, 3 or 4 in which hydrofluoric acid is used as the solvent in an amount of 15 to 50 mols per mol of 3-anilinopropionic acid.

6. A process according to claim 1 for the preparation of a 1,2,3,4-tetrahydroquinolin-4-one of the general formula:

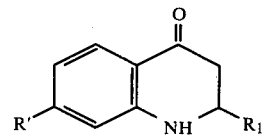

(wherein R' represents a halogen atom, a straight- or branched-chain alkyl radical containing 1 to 4 carbon atoms or a straight- or branched-chain alkoxy radical containing 1 to 4 carbon atoms, and $R_1$ is as defined in claim 1) virtually free of the isomer in the 5-position, which comprises cyclising a 3-anilinopropionic acid of the general formula:

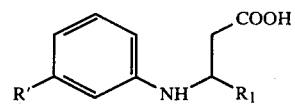

(wherein R' and $R_1$ are as hereinbefore defined) in a mixture of hydrofluoric acid and boron trifluoride, and isolating the product obtained.

7. A process according to claim 1 for the preparation of 7-chloro-1,2,3,4-tetrahydroquinolin-4-one virtually free of 5-chloro-1,2,3,4-tetrahydroquinolin-4-one which comprises cyclising 3-m-chloroanilinopropionic acid in a mixture of hydrofluoric acid and boron trifluoride, and isolating the quinolinone product obtained.

8. A process according to claim 7 which comprises cyclising 3-m-chloroanilinopropionic acid in a solution, saturated with boron trifluoride, in hydrofluoric acid, in amounts of one molecule of 3-m-chloroanilinopropionic acid per 15 to 50 mols of hydrofluoric acid, under a pressure of between 1 and 30 bars and at a temperature between 20° and 100° C.

9. A process according to claim 8 in which the pressure is between 2 and 16 bars and the temperature is between 70° and 90° C.

10. A process according to claim 7, 8 or 9 in which at least 2 mols of boron trifluoride are used per mol of 3-m-chloroanilinopropionic acid.

* * * * *